United States Patent [19]

Yoshihara et al.

[11] Patent Number: 4,940,578
[45] Date of Patent: Jul. 10, 1990

[54] HAIR PREPARATION

[75] Inventors: Toru Yoshihara; Jiro Kawase, both of Funabashi; Yukihiro Fukuyama, Wakayama, all of Japan

[73] Assignee: Kao Corporation, Tokyo, Japan

[21] Appl. No.: 202,983

[22] Filed: Jun. 3, 1988

[30] Foreign Application Priority Data

Jun. 18, 1987 [JP]  Japan .................................. 62-152376
Jun. 18, 1987 [JP]  Japan .................................. 62-152377

[51] Int. Cl.$^5$ ........................ A61K 7/06; A61K 7/075
[52] U.S. Cl. ..................................... 424/70; 424/78; 252/DIG. 13
[58] Field of Search ................. 424/70, 78; 514/852, 514/869, 880, 881; 252/DIG. 13

[56] References Cited

U.S. PATENT DOCUMENTS 4,246,257  1/1981  Elliott et al. ......................... 424/78
4,489,058  12/1984  Lay et al. ......................... 424/81 X
4,664,910  5/1987  Caserio et al. ......................... 424/70
4,735,797  4/1988  Grollier et al. ..................... 424/78 X

FOREIGN PATENT DOCUMENTS 1040750  10/1958  Fed. Rep. of Germany .
2549369   1/1985  France .
  80499   5/1982  Japan .................................... 424/70

Primary Examiner—Ellis P. Robinson
Assistant Examiner—Susan S. Rucker
Attorney, Agent, or Firm—Flynn, Thiel, Boutell & Tanis

[57] ABSTRACT

A hair preparation comprises an oil-absorptive polymer of a vinyl monomer having a solubility parameter of 7 to 10, said polymer being porous and having a squalene absorption of at least 1 ml/g. It may further contain an anti-dandruff agent. The hair preparation may also comprise an anti-dandruff agent and a different oil-absorptive substance.

11 Claims, No Drawings

HAIR PREPARATION

The present invention relates to hair preparations which have a high sebum absorptivity and are capable of making the users comfortable during the use thereof and reduces greasiness of the scalp and hair.

It also relates to hair preparations comprising an anti-dandruff agent and a specified oil-absorptive substance capable of absorbing sebum.

PRIOR ART

Although sebum makes the skin and hair glossy and smooth when the secretion thereof is proper, it also makes the skin and hair greasy and sticky when secreted excessively. Furthermore, the application of makeup to a face is also impaired by sebum. In addition, the apparent volume of hair is reduced by excessive sebum which makes the keeping of a beautiful hairstyle impossible. Although excessively secreted sebum can be easily removed by washing, it will become excessive again within several hours on the skin and within several days on the scalp and the hair and, therefore, repeated washings are necessitated.

Under these circumstances, studies are in progress for the purpose of physiologically controlling the secretion of sebum or physically absorbing excessive sebum with a powder.

However, the former method is not employed practically, since no safe and effective medicine has been found yet.

Although the latter method, wherein sebum is physically absorbed by a powder, has no serious problem of safety, it has still problems in that the sebum absorptivity is insufficient and that the users do not feel comfortable during its use.

For example, a process for controlling the secretion of sebum with an inorganic powder, such as a clay mineral or an oxide is described in Japanese Patent Laid-Open No. 65807/1986. However, porous or bedded inorganic substances usually have a defect in that the oil absorptivity thereof is seriously reduced by sweat or dirts.

A method of reducing seborrhea with a silylated silica gel is described in Japanese Patent Laid-Open No. 144710/1984. In this method, the surfaces of the inorganic powdery particles are made hydrophobic and the sebum is absorbed in interparticle spaces of aggregates of the primary particles. No high oil absorptivity can be expected by this method U.S. Pat. No. 4,489,058 discloses a method of absorbing sebum with a copolymer of styrene and stearyl methacrylate which has a high compatibility with sebum, by swelling in order to keep the skin free from acne. Although this method is excellent in that the sebum can be absorbed in the presence of sweat or dirts, the amount of absorbtion is still insufficient and the touch of the skin after absorption of the sebum is poor, since the sebum is absorbed by mere swelling. Another defect of this method is that the copolymer adheres to hair, since it has an average particle diameter of around 150 $\mu$m.

Various anti-dandruff agents are incorporated in hair preparations such as shampoos, rinses and hair tonics in order to prevent dandruff formation and the itching of the scalp. All of them have an antibiotic activity and activities of dissolving a corneous layer or controlling the metabolic rate of this layer on the scalp. As a result, dandruff formation is prevented. However, it has been pointed out that daily use of an anti-dandruff agent exerts a significant effect on the physical properties of hair. Namely, hair becomes greasy and sticky soon after shampooing [see, for example, International Journal of Cosmetic Science, 5, 77 (1983)].

The mechanism of the phenomenon by which hair becomes greasy after the daily use of the anti-dandruff agent-containing composition has not yet been fully understood. In this connection, an anti-dandruff composition also having an effect of inhibiting or retarding the onset of greasiness has not been developed.

As for special oil-absorptive substances capable of absorbing sebum, for example, colloidal silica is described in Japanese Patent Publication No. 20793/1971 and a combination of a hydroxycholanic acid derivative and a powdery oil absorbent is disclosed in European Patent No. 58000. They are used as raw material for the skin cosmetics. However, an anti-dandruff composition suitable for controlling or retarding the onset of greasiness has not been reported.

After clinical analysis of the tendency of sebum to diffuse toward hair as a result of the repeated use of ordinary anti-dandruff agents, made for the purpose of overcoming the defect that the hair becomes greasy at an early stage when the ordinary anti-dandruff agent is used every day, the inventors have found that the secreted sebum is distributed to the surface of the scalp and then to the hair after the lapse of days, more precisely the sebum reaches saturation on the surface of the scalp quickly in one or two days and then the diffusion thereof toward the hair begins, that the fragments of a corneous layer on the surface of the scalp, i.e., dandruff, play an important role as a sebum reservoir structure, that a decrease in the dandruff due to the effect of the anti-dandruff agent brings about a decrease in the amount of the sebum stored on the scalp surface and an increase, on the contrary, in the diffusion rate of the sebum toward hair, and that this phenomenon occurs rapidly, even one day after shampooing and thereafter.

SUMMARY OF THE INVENTION

After intensive investigations made for the purpose of overcoming the above-described defects, the inventors have found that the problems can be solved by using a porous, oil-absorptive vinyl polymer. The present invention has been completed on the basis of this finding.

The inventors have surmised that when a new sebum reservoir structure is formed as a substitute for the fragment of a corneous layer, which are unfavorable from the viewpoint of beauty, on the scalp surface and/or hair surface, the development of the greasiness can be delayed or eliminated. After intensive investigations made for the purpose of developing a means of forming the sebum reservoir structure, the inventors have found that when an anti-dandruff composition, comprising a carrier far smaller than said dandruff and having a sebum absorptivity higher than that of said dandruff, is used, the dandruff and itch can be prevented, controlled and/or relieved and, in addition, the onset of greasiness can be retarded, a problem that could not be solved in the prior art.

The present invention has been completed on the basis of the above-described findings. The present invention provides new hair preparations, based on a new idea, unlike ordinary anti-dandruff compositions. The new hair preparations have the remarkable effect of preventing or removing dandruff and itch and controlling the greasiness of hair.

The invention provides a hair preparation which comprises an oil-absorptive polymer of a vinyl monomer having a solubility parameter of 7 to 10, said polymer being porous, having a squalene absorption of at least 1 ml/g. It may further contain an anti-dandruff agent. It also comprises an anti-dandruff agent and another oil-absorptive substance.

A hair preparation of the invention comprises an oil-absorptive polymer of a vinyl monomer having a solubility parameter of 7 to 10, said polymer being porous and having a squalene absorption of at least 1 ml/g, and a carrier.

It is preferable that the hair preparation comprises 0.05 to 5 percent by weight of the oil-absorptive polymer and the balance being the carrier. It is also preferred that the oil-absorptive polymer have an average particle size of 0.005 to 30 microns and have such a size distribution that it contains 90 percent by weight or more of particles having sizes in the range of 0.005 to 30 microns.

The invention also provides a hair preparation which comprises 0.01 to 10 percent by weight of an anti-dandruff agent, 0.05 to 5 percent by weight of an oil-absorptive substance in the form of fine particles and having a squalene absorption of at least 0.5 ml/g in the dried state and the balance being a carrier.

It is preferable that the oil-absorptive substance be the above defined oil-absorptive polymer.

Initially, the composition comprising the oil-absorptive polymer will be explained below in detail.

The present invention provides hair preparations characterized by comprising an oil-absorptive polymer having a squalene absorption of at least 1 ml/g which is prepared by polymerizing one or more vinyl monomers having a solubility parameter of 7 to 10 and making the formed polymer porous.

The oil-absorptive polymer according to the present invention has an average particle diameter of 0.005 to 30 μm. Preferably the polymer comprises at least 90 wt.% of particles having a diameter of 0.005 to 30 μm and is crosslinked. The porous polymer is prepared preferably by dissolving the monomer in a nonpolymerizable organic solvent, suspending, dispersing or emulsifying the solution in water, conducting polymerization and thereafter removing the organic solvent.

The polymerization can be conducted by any known method such as suspension, dispersion or emulsion polymerization. Suspension polymerization is recommended when a polymer having a particle diameter 10 μm or larger is desired. Dispersion polymerization and emulsion polymerization are recommended when it is desired for the polymer to have particle diameters of 1 to 10 μm and 1 μm or less, respectively. From the viewpoints of the touch of the skin and hair after application of the preparation and adhesion of the particles, smaller particles are preferred. However, emulsion polymerization has a defect in that a surfactant used in a relatively large amount therein cannot be removed easily.

The polymer can be made porous by removing nonpolymerizable substances such as an organic solvent, plasticizer and linear polymer contained in the polymerization solution after the completion of the polymerization. A particularly preferred process comprises dissolving the monomer in a nonpolymerizable organic solvent which is a good solvent for the monomer but a poor solvent for the polymer formed, suspending, dispersing or emulsifying the monomer solution in water, polymerizing it and removing the organic solvent after completion of the polymerization.

The monomers usable in the present invention are vinyl monomers having a solubility parameter of 7 to 10. They include, for example, esters of methacrylic acid with higher alcohols having 8 to 24 carbon atoms, esters of acrylic acid with higher alcohols having 8 to 24 carbon atoms, styrene, styrene derivatives having a straight-chain or branched hydrocarbon substituent having 1 to 12 carbon atoms, vinyl esters of unsaturated carboxylic acids having 8 to 20 carbon atoms, acrylic acid, methacrylic acid and diolefins having 4 to 6 carbon atoms. When the solubility parameter of the vinyl monomer is outside the range of 7 to 10, the compatibility of the product with sebum is poor and, therefore, sufficient sebum absorptivity cannot be obtained.

These monomers can be used either alone or in the form of a combination of two or more of them.

When a monomer having a long-chain alkyl group, such as stearyl methacrylate, is used singly, the polymer will have a low glass transition point Tg and a low porosity, even though it has a high compatibility with sebum. In such a case, the monomer is preferably copolymerized with a comonomer capable of forming a polymer having a Tg of 100° C. (373° K.) or higher, such as styrene.

Examples of particularly preferred monomers include esters of a higher alcohol having 8 to 24 carbon atoms, such as stearyl alcohol, with acrylic or methacrylic acid. Although they can be homopolymerized, it is preferred to copolymerize the monomer with styrene per se or styrene substituted with a straight-chain or branched alkyl group having to 12 carbon atoms capable of forming a polymer having a Tg of 100° C. (373° K.) or higher in order to further increase the porosity and oil absorptivity (refer to Preparation Examples 1 and 2). The weight ratio of the acrylate or methacrylate to styrene or its derivative to be copolymerized is preferably at least 30/70. When this ratio is less than 30/70, the polymer becomes hard and, therefore, the touch thereof becomes unfavorably poor.

To obtain an excellent touch, it is preferred that the oil-absorptive polymer according to the present invention be swellable with sebum but insoluble therein. Therefore, the polymer is preferably crosslinked. Crosslinking is conducted by a process wherein a polyfunctional monomer is added during the polymerization, a crosslinking process or a selfcrosslinking process. The polyfunctional monomers include, for example, polyvinyl aromatic compounds such as divinylbenzene, polyvinyl heterocyclic compounds such as divinylpyridine, dimethacrylates such as ethylene glycol dimethacrylate and triethylene glycol dimethacrylate, and diacrylates such as ethylene glycol diacrylate and triethylene glycol diacrylate. The amount of the crosslinking agent is preferab,ly 50 wt.% or below based on the polymer When the amount of crosslinking agent exceeds 50 wt.%, the swellability of the polymer is seriously inhibited. A particularly preferred amount of the crosslinking agent is 0.01 to 50 wt.% based on the total polymer.

The organic solvents used in for making the polymer porous in the present invention include, for example, aromatic compounds such as toluene and benzene, esters such as ethyl acetate and butyl acetate, alcohols such as isoamyl alcohol and methylisobutyl carbinol, saturated hydrocarbons such as n-hexane, n-octane and n-dodecane, and halogenated solvents such as dichloroethane and trichloroethylene. Among them, those which are good solvents for the vinyl monomers having a solubility parameter of 7 to 10 and which are poor solvents for the polymers prepared from these monomers are particularly preferred. The preferred solvents include, for example, aliphatic hydrocarbons such as hexane, octane and dodecane, and aromatic hydrocarbons such as toluene and benzene The weight ratio of the monomer to the organic solvent is preferably 1/1 to ¼.

The plasticizers are, for example, dioctyl phthalate and dibutyl adipate. The linear polymers are, for example, polystyrene and polyvinyl acetate.

The polymerization initiators used are ordinarily oil-soluble ones. They include, for example, peroxides and azo compounds such as benzoyl peroxide, lauroyl peroxide, 2,2'-azobisisobutyronitrile, 2,2'-azobis-(2,4-dimethylvaleronitrile), o-chlorobenzoyl peroxide and o-methoxybenzoyl peroxide.

The dispersion and emulsion stabilizers usable in the present invention are those commonly used in the art. They include, for example, water-soluble polymers such as starch, hydroxyethylcellulose, carboxymethylcellulose, polyvinylpyrrolidone, polyvinyl alkyl ethers and polyvinyl alcohols; barely water-soluble inorganic salts such as barium sulfate, calcium sulfate, barium carbonate, calcium carbonate, magnesium carbonate and calcium phosphate; and surfactants such as sodium lauryl sulfate, sodium cetyl sulfate and sodium polyoxyethylene lauryl ether sulfate.

The monomer solution comprising the monomer(s), a diluent (an agent for making the polymer porous) and a polymerization initiator is dispersed or suspended in water in the presence of the above-mentioned dispersion or emulsion stabilizer by a known process to form droplets and then polymerization is conducted to prepare the intended porous polymer. In this process, the monomer solution is dispersed or suspended by an ordinary method such as an ordinary stirring method with any of various ordinary stirrers or a forced stirring method with a homogenizer or by irradiation with ultrasonic waves. These means are selected suitably to obtain particles having desired particle diameters. The proper polymerization temperature varies depending on the polymerization initiator used. It is usually in the range of 20° to 95° C. As a matter of course, the polymerization temperature must be lower than the boiling points of the monomer(s) and diluent under atmospheric pressure.

After completion of the polymerization, the polymer particles are separated by filtration. The aqueous phase is removed. The polymer particles are washed with water and/or with a solvent in order to replace the diluent having a high boiling point with the solvent having a lower boiling point. The product is then pulverized by an ordinary method such as spray-drying or reduced-pressure drying.

Before the polymerization, the mixture is in the form of droplets of a homogeneous solution comprising the monomer(s), diluent and initiator. As the polymerization proceeds, however, the diluent, which is a poor solvent for the polymer(s), causes microscopic phase separation and is then vaporized (desorbed) during drying under reduced pressure to form the intended porous polymer.

The oil absorption of the oil-absorptive polymer is determined by the "Method of Measurement of Oil Absorption of Pigment" stipulated in JIS K 5101 (1978) using squalene as the oil. In this method, 1 g of the powder is placed on a glass plate and kneaded by means of a spatula while squalene is gradually added dropwise thereto until the powder is wholly converted into a paste. The amount of squalene (ml) required per gram of the powder is referred to as the absorption. Although boiled linseed oil is used in JIS, squalene is used in the process of the present invention, since it is close in properties to sebum. The absorption of the polymer according to the present invention is at least 1 ml/g, preferably at least 2 ml/g. The porosity can be determined in terms of the pore volume determined from the pore distribution measured by mercury porosimetry. The detail of this method is described in, for example, "Funtai Kogaku Binran" edited by Funtai Kogaku-kai and published by Nikkan Kogyo Shinbun-sha in 1986. The pore volume is at least 0.1 ml/g, preferably at least 0.15 ml/g.

The porous oil-absorptive polymer thus prepared can be dispersed in water, a lower alcohol or a mixture thereof to form a dispersion usable as a hair lotion The most preferred base of the hair preparation of the present invention is a mixture of water with ethanol in a weight ratio of 99/1 to 20/80, preferably 95/5 to 40/60. The amount of the oil-absorptive polymer in the hair lotion is preferably 0.05 to 5 wt.%, particularly 0.1 to 2 wt.%.

The lotion can contain further various water-soluble polymers in order to stabilize the dispersion or to dress the hair. They include nonionic water-soluble polymers such as polyvinyl alcohol, polyvinylpyrrolidone and hydroxyethylcellulose; and anionic water-soluble polymers such as carboxymethylcellulose, crosslinked polyacrylic acid (carboxyvinyl polymer), xanthan gum and guar gum. These polymers are used in an amount of preferably 0.01 to 5 wt.%, particularly 0.05 to 1 wt.%.

The hair preparation of the present invention may contain, in addition to the above-described components, such other ordinary components in such amounts that they do not damage the effect of the present invention. They include, for example, polyhydric alcohols, e.g. glycerol, dipropylene glycol and 1,3-butylene glycol, nonionic surfactants, cationic surfactants, anionic surfactants, dyes, antiseptics, flavors, antioxidants, chelating agents, germicides, medicinal preparations, e.g. vitamins and hormones, astringents and U.V. absorbers.

The porous vinyl polymer contained in the hair preparation of the present invention has a far higher capacity of absorbing squalene than that of ordinary inorganic powders and water-insoluble polymers. Therefore, the hair preparation containing the porous vinyl polymer exhibits an excellent effect of reducing the greasiness as will be shown in the following Examples.

A composition comprising an anti-dandruff agent and an oil-absorptive substance will be explained below in detail.

The present invention provides hair preparations characterized by comprising 0.01 to 10 wt.% of an anti-dandruff agent and 0.05 to 5 wt.% of an oil-absorptive substance in the form of fine particles and having a squalene absorption of at least 0.5 ml/g in a dried state.

The anti-dandruff agents usable in the present invention are well known ones. They include, for example, polyvalent metal salts of 2-mercaptopyridine N-oxide, colloidal sulfur, sulfur-containing amino acids and salts of them described in Japanese Patent Laid-Open No. 183614/1983, 2,2'-dithiobispyridine 1,1'-dioxide of the formula (I):

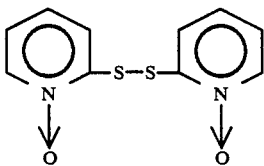

(I)

and hydrates of metal salts thereof, such as magnesium sulfate, 1-hydroxy-2-pyridone derivatives of the general formula (II):

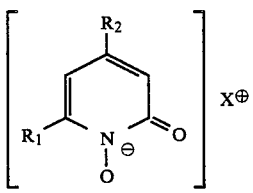

(II)

,wherein $R_1$ represents an alkyl group having 1 to 17 carbon atoms, an alkenyl group having 2 to 17 carbon atoms, a cycloalkyl group having 5 to 8 carbon atoms, a bicycloalkyl group having 7 to 9 carbon atoms, a cycloalkylalkyl group in which the alkyl group has 1 to 4 carbon atoms and the cycloalkyl group may be substituted with an alkyl group having 1 to 4 carbon atoms, an aryl group, an aralkyl group in which the alkyl group has 1 to 4 carbon atoms, an arylalkenyl group in which the alkenyl group has 2 to 4 carbon atoms, an aryloxyalkyl group or an arylmercaptoalkyl group in which the alkyl group has 1 to 4 carbon atoms, a benzhydryl group, a phenylsulfonylalkyl group in which the alkyl group has 1 to 4 carbon atoms, a furyl or furylalkenyl group in which the alkenyl group has 2 to 4 carbon atoms (the aryl residue in each of the above-mentioned groups may be substituted with an alkyl or alkoxy group having 1 to 4 carbon atoms, a nitro group, a cyano group or a halogen atom), $R_2$ represents a hydrogen atom, an alkyl group having 1 to 4 carbon atoms, an alkenyl or alkynyl group having 2 to 4 carbon atoms, a halogen atom, a phenyl group or a benzyl group, and X represents a residue of an organic amine,
described in Japanese Patent Publication No. 39805/1983, salicylic acid and its derivatives, triethyl citrate, described in Japanese Patent Laid-Open No. 180417/1983, indole derivatives of the general formula (III):

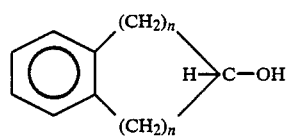

(III)

,described in West German Patent No. 3142296, compounds of the general formula (IV):

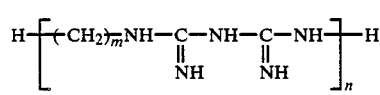

(IV)

wherein m represents a number of 1 to 10 and n represents a number of 1 to 6, and salts thereof described in West German Patent No. 012767, 2-oxotetrahydro-1,3,5-thiadiazine derivatives of the general formula (V):

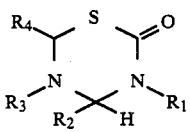

(V)

,described in west German Patent No. 3022799, ω-(aminothiocarbonylmercapto)alkanoic acids, described in Belgian Patent No. 2085728, compounds of the general formula (VI):

$$R-NHC(S)-S-(CH_2)_n COOH \qquad (VI)$$

and salts thereof, quinone derivatives, selenium disulfide, phenol derivatives and coal tar.

Among them, the polyvalent metal salts of 2-mercaptopyridine, 2,2'-dithiobispyridine 1,1'-dioxide of the formula (I) and 1-hydroxy-2-pyridone derivatives of the general formula (II) are preferred from the viewpoints of the safety and effectiveness. Particularly preferred are the zinc salt of 2-mercaptopyridine (zinc pyrithione), the triethanolamine salt of 1-hydroxy-4-methyl-6-(2,4,4-trimethylpentyl)-2(1H)-oyridone (Piroctone Auramine) and 2,2'-dithiobispyridine 1,1'-dioxide. The zinc salt of 2-mercaptopyridine is used preferably in the form of fine particles, at least 50 wt.% of which have a particle diameter of 0.2 μm or less and which have an average particle diameter of 0.2 μm or less, as described in Japanese Patent Laid-Open Nos. 16972/1985, 16973/1985 and 224676/1985.

The oil-absorptive substance in the form of fine particles used in the present invention has a particle size (0.005 to 30 μm on average) far smaller than the ordinary fragment of a corneous layer and an oil absorption comparable to that of the fragment in a dried state (1 ml.squalene/g). The oil-absorptive substance of the present invention comprises, for example, at least one of the following oil-absorptive substances (i) to (iii) in the form of fine particles and has an oil absorption as high as at least 0.5 ml squalene/g (determined by the "Method of Measurement of Oil Absorption" of JIS K 5101). Such a high oil absorption is obtained by reducing the particle size.

(i) natural clay minerals (such as kaolin, talc, mica, sericite and bentonite) and synthetic inorganic compounds (such as phyllosilicates and platy silicates containing alkali and alkaline earth metals, e.g. Na, K, Al and Ca and fluorine, colloidal silica gel, zeolite and magnesium carbonate), as well as those which have been subjected to a surface modification treatment, a chemical treatment making them porous or a treatment for controlling the particle diameter in order to increase the oil absorptivity, to control the oil absorptivity/water absorptivity and to increase the selectivity toward the oil to be absorbed, (ii) natural and synthetic organic polymers (such as nylon, polyethylene, polypropylene, polystyrene, urea resin, porous vinyl polymer, copolymers of divinylbenzene, copolymers prepared from a polyfunctional crosslinking agent as a comonomer, and pulp) and those having a modified surface, internal structure, pore diameter, porosity, dynamic specific volume, particle diameter, surface area and wettability modified by various methods, and (iii) composite materials based on the substances of the above items (i) and (ii) (such as a porous polymer having the surface treated with an inorganic compound, e.g. $SiO_2$ or $TiO_2$ or, contrarily, inorganic carriers having their surface treated with an organic compound).

Among the oil-absorptive substances in the form of fine particles, bentonite mainly comprising montmorillonite, colloidal silica and porous vinyl polymers are preferred. From the viewpoint of oil absorptivity, touch and adhesion to the skin, the most preferred is a porous vinyl polymer prepared from one or more vinyl monomers having a solubility parameter of 7 to 10. Typical examples of the vinyl monomers having a solubility parameter of 7 to 10 include esters of methacrylic or acrylic acid with a higher alcohol having 8 to 24 carbon atoms, styrene and styrene derivatives having an alkyl substituent having 1 to 12 carbon atoms. A particularly preferred vinyl monomer is a mixture of acrylate or methacrylate with styrene or styrene derivative in a weight ratio of 30/70 or higher. The porous polymer can be prepared by mixing the monomer, or a mixture of the monomers, with a nonpolymerizable organic solvent such as a volatile aliphatic hydrocarbon, e.g. n-hexane, n-octane or n-dodecane, or an aromatic hydrocarbon such as benzene or toluene, in a weight ratio of the monomer(s) to the organic solvent of 1/1 to ¼, subjecting the mixture to dispersion, suspension or emulsion polymerization in water and removing the nonpolymerizable organic solvent.

The polymer is preferably crosslinked with a polyfunctional monomer, for example, a polyvinyl aromatic compound such as divinylbenzene, a polyvinyl heterocyclic compound such as divinylpyridine, a dimethacrylate such as ethylene glycol dimethacrylate or triethylene glycol dimethacrylate, or a diacrylate such as ethylene glycol acrylate or triethylene glycol acrylate. The amount of the crosslinking agent is preferably 50 wt.% or less based on the polymer. When the amount of crosslinking agent exceeds 50 wt.%, the swellability of the polymer is seriously reduced. A particularly preferred amount of the crosslinking agent is 0.01 to 50 wt.% based on the polymer.

The most preferred vinyl polymer used in the present invention is prepared by polymerizing a mixture of stearyl methacrylate, styrene, divinylbenzene and toluene in water and then making the formed polymer porous.

The oil absorption of the oil-absorptive fine particles is determined by the "Method of Measurement of Oil Absorption of Pigment" according to JIS K 5101 (1978) using squalene as the oil in the present invention. In this method, 1 g of the powder is placed on a glass plate and kneaded by means of a spatula while squalene is gradually added dropwise thereto until the powder is wholly converted into a paste. The amount of squalene (ml) required per gram of the powder is referred to as the absorption. Although boiled linseed oil is used in JIS, squalene is used in the process of the present invention, since it is closer in properties to sebum.

The oil-absorptive substances determined by the above-mentioned method is shown in Table 1, wherein squalene is used as the oil.

TABLE 1

| Oil-absorptive substance | Oil absorption (ml/g) |
|---|---|
| synthetic phyllosilicate [$Mg_3(Si_4O_{11})H_2O.11H_2O$] | 1.07 |
| synthetic phyllosilicate [$K_2O.3Al_2O_3.6SiO_2$] | 0.99 |
| synthetic platy silicate [$Ca_4(Si_6O_{16})(OH).4H_2O$] | 4.96 |
| synthetic platy silicate [$Ca_4(Si_6O_{16})(OH)(OH)$] | 5.09 |
| dry synthetic platy silicate [$Ca(Si_6O_{16})(OH)$] | 1.40 |
| porous colloidal silica having a pore diameter of 120 Å [$SiO_2.nH_2O$] | 1.52 |
| porous colloidal silica having a pore diameter of 60 Å [$SiO_2.nH_2O$] | 1.38 |
| Talc JA46A | 0.54 |
| Kaolin A | 0.72 |
| bentonite mainly comprising montmorillonite | 0.86 |
| spherical colloidal silica [Aerosil 200] | 5.00 |
| spherical colloidal silica [Aerosil 130] | 5.38 |
| porous nylon beads [Orgasol 2000D] | 0.80 |
| non-porous nylon beads [Toray Nylon SP500] | 0.57 |

The hair preparation of the present invention may be in either solid or liquid form. A liquid suspension of the oil-absorptive substance in the form of fine particles is preferably used. The liquid in which the anti-dandruff agent and the oil-absorptive fine particles of the present invention are suspended can be, for example, water, a lower alcohol or a mixture of them. When the hair preparation in solid form is applied to the scalp and hair and rubbed thereinto, it becomes a liquid to uniformly and effectively spread the anti-dandruff agent and the oil-absorptive agent on the surfaces thereof. The solid hair preparation is desirably in the form of gel, paste or the like. It can be used easily when it contains a substantial amount of a solvent. The alcohols used as the solvent are preferably lower monohydric alcohols and some of them may be replaced with a dihydric or polyhydric alcohol. The monohydric alcohols usable in the present invention are preferably ethanol and isopropanol. Mixtures of two or more components selected from the group consisting of ethanol, isopropanol, water and other monohydric, dihydric and polyhydric alcohols can also be used. The anti-dandruff agent can be suspended or dissolved also therein.

To keep the suspension of the oil-absorptive substance homogeneous, an organic gum can be used. The organic gums include, for example, carboxymethylcellulose, hydroxyalkylcellulose, carboxypolymethylene, polyvinylpyrrolidone, acrylates, gelatin, dextrin, tragacanth, acacia, alginic acid, pectin and carrageenan.

The hair preparation of the present invention may contain various other components for various purposes. They include, for example, ordinary colorants such as dyes and pigments, flavors, vitamins, hair growth promoting agents and surfactants.

The hair preparation of the present invention is a new one prepared on the basis of a new conception unlike ordinary anti-dandruff compositions. The hair preparation is effective in preventing dandruff and itch and also in preventing hair from becoming greasy, which were problems with the ordinary anti-dandruff compositions.

The following Preparation Examples and Examples will further illustrate the present invention, but by no means limit the invention.

PREPARATION EXAMPLE 1

40 g of stearyl methacrylate, 40 g of divinylbenzene, 80 g of toluene, 2 g of benzoyl peroxide and 700 g of a 0.6% aqueous polyvinyl alcohol solution were placed in a 2-1 separable flask and mixed by means of a homomixer at 11,000 rpm for 5 min. Then the dispersion thus obtained was stirred at 300 rpm at 80° C. for 8 h in a nitrogen atmosphere to conduct polymerization. After completion of the polymerization, the reaction mixture was filtered. The filtration residue was washed with water and then with acetone and dried to obtain 40 g of a porous vinyl polymer having an average particle diameter of 6.7 μm.

According to the results of the determination of the pore distribution by mercury porosimetry, the polymer had pores of smaller than 347 Å on their particle surfaces and a pore volume of 0.15 ml/g.

PREPARATION EXAMPLE 2

20 g of stearyl methacrylate, 20 g of styrene, 40 g of divinylbenzene, 30 g of toluene, 90 g of n-dodecane, 0.8 g of benzoyl peroxide and 470 g of a 3.3% aqueous sodium dodecylsulfate solution were placed in a 2-1 separable flask and stirred at 300 rpm at 65° C. for 9 h in a nitrogen atmosphere to conduct polymerization. After completion of the polymerization followed by the same procedure at that of Preparation Example 1, 50 g of a porous vinyl polymer having an average particle diameter of 2.0 μm was obtained.

According to the results of the determination of the pore distribution by mercury porosimetry, the polymer had pores of smaller than 725 Å on their particle surfaces and a pore volume of 0.299 ml/g.

PREPARATION EXAMPLE 3

17 g of stearyl methacrylate, 17 g of divinylbenzene, 34 g of toluene, 1 g of potassium persulfate and 530 g of 1.0% aqueous polyoxyethylene (35 mol of ethylene oxide added) nonylphenyl ether were placed in a 2-1 separable flask and stirred at 300 rpm at 5° C. for 8 h in a nitrogen atmosphere to conduct polymerization. After the completion of the polymerization, followed by topping conducted under 100 to 150 mmHg for 2 to 3 h, a porous vinyl polymer was obtained in the form of an aqueous suspension. The average particle diameter of the polymer was smaller than 9.7 μm.

PREPARATION EXAMPLE 4

A porous vinyl polymer having an average particle diameter of 2.5 μm was prepared in the same manner as in Preparation Example 2 except that 20 g of styrene was replaced with 20 g of t-butylstyrene and the amount of divinylbenzene was altered from 40 g to 0.4 g.

PREPARATION EXAMPLES 5 AND 6

A vinyl polymer was prepared in the same manner as that of Preparation Example 1 except that the amount of toluene was altered to 160 g (Preparation Example 5) or no toluene was used (Preparation Example 6).

The polymer thus prepared in Preparation Example 6 was a comparative one.

The oil absorptivity of the polymers prepared in the above Preparation Examples 1 to 6 was determined according to the above-mentioned method based on JIS K 5101. For comparison, the oil absorptivity of talc, kaolin and Polymer No. 14 in Example 1 of U.S. Pat. No. 4,489,058 which has the highest oil absorptivity among all the polymers mentioned in the specification of this patent and which comprises 65 wt. % of t-butylstyrene, 35 wt. % of stearyl methacrylate and 0.0125 wt. % of divinylbenzene as the crosslinking agent was determined.

The results are shown in Table 2.

TABLE 2

| | Squalene absorption (ml/g) |
|---|---|
| Preparation Example 1 | 2.0 ± 0.1 |
| Preparation Example 2 | 3.3 ± 0.3 |
| Preparation Example 3 | 3.0 ± 0.1 |
| Preparation Example 4 | 2.5 ± 0.1 |
| Preparation Example 5 | 2.9 ± 0.1 |
| Preparation Example 6 | 0.6 ± 0.1 |
| polymer No. 14 of U.S. Pat. No. 4 489 058 | 0.6 ± 0.1 |
| talc | 0.5 ± 0.1 |
| kaolin | 0.5 ± 0.1 |

EXAMPLE 1

Scalp Lotions A and B and Comparative Lotions C and D (controls) having compositions shown in Table 3 were prepared.

Piroctone Auramine [1-hydroxy-4-methyl-6-(2,4,4-trimethylpentyl)-2(1H)-pyridone triethanolamine salt] is an anti-dandruff agent of Hoechst (trade name: Octopirox). It has been commercially used in the fields of shampoos, rinses and hair tonics and its effect has already been recognized. Bentonite is an inorganic bedded clay mineral mainly comprising montmorillonite and usable as a carrier having a relatively high oil absorptivity. Bentonite having a primary particle diameter of around 2 μm (sebum absorption: 0.86 ml squalene/g) was used. The spherical primary particles of the colloidal silica used had a particle diameter of around 12 mμ (sebum absorption: 5 ml squalene/g).

TABLE 3

| Formulation | Scalp lotion A (present invention) | Scalp lotion B (present invention) | Scalp lotion C (comp.) | Scalp lotion D (comp.) |
|---|---|---|---|---|
| bentonite mainly comprising montmorillonite | 0.2 wt % | — | — | — |
| colloidal silica (Aerosil 200) | — | 0.2 | — | — |
| Piroctone Auramine | 0.2 | 0.2 | 0.2 | — |
| lactic acid | proper amt. | proper amt. | proper amt. | proper amt. |
| flavor | proper amt. | proper amt. | proper amt. | proper amt. |
| hydroxyethyl-cellulose | 0.05 | — | 0.05 | 0.05 |
| ethanol | 50 | — | 50 | 50 |
| isopropanol | — | 50 | — | — |
| purified water | balance | balance | balance | balance |
| pH adjustment | 6~7 | 6~7 | 6~7 | 6~7 |

Ten male subjects (aged 18 to 25), previously to be suffering from dandruff and itch, were divided into two groups and subjected to a clinical test using the scalp lotions A and B prepared as described above and comparative scalp lotions C and D for 6 weeks.

In the clinical test, the scalp lotion D (control) was used in the first and second weeks, the scalp lotion C was used in the third and fourth weeks and the scalp lotion A (for five subjects in group 1) or scalp lotion B (for five subjects in group 2) was used in the fifth and sixth weeks. In practice, they shampooed with the control shampoo three times a week (on Monday, Wednesday and Friday). In each case, after shampooing with a control shampoo followed by drying with a towel, about 4 g of the scalp lotion was spread over the scalp. On Monday, after two weeks, the formation of dandruff and the development of greasiness of the hair were judged by the panellists and classified into four ranks. The results are shown in Table 4.

TABLE 4

| Scalp lotion | Dandruff | Greasiness |
|---|---|---|
| D | 2.8 | 1.8 |
| C | 0.6 | 2.8 |
| B | 0.4 | 0.8 |
| A | 0.4 | 0 |

Notes
0: scarcely observed
1: slightly observed
2: observed
3: considerably observed.

It is apparent from Table 4 that the scalp lotions A and B of the present invention exhibit remarkable effects in the prevention of the formation of dandruff and control of greasiness.

EXAMPLE 2

Scalp treatments (to be used in a shampoo-free condition) A and B of the present invention and comparative scalp treatments C, D and E having the compositions shown in Table 5 were prepared.

TABLE 5

| Formulation | Present invention | | Comparative | | |
|---|---|---|---|---|---|
| | A | B | C | D | E |
| porous vinyl polymer prepared in Preparation Example 4 | 0.3 wt % | 0.3 | 0.3 | — | — |
| Carbopol 941*1 | 0.18 | 0.18 | 0.18 | 0.18 | 0.18 |
| Silicone KF352A*2 | 0.1 | 0.1 | 0.1 | 0.1 | 0.1 |
| triethanolamine | proper amt. | proper amt. | proper amt. | proper amt. | proper amt. |
| 2-amino-2-methyl-1-propanol | proper amt. | proper amt. | proper amt. | proper amt. | proper amt. |
| Octopirox*3 | 0.1 | — | — | — | — |
| zinc pyrithione (Zpt) | — | 0.1 | — | 0.1 | — |
| ethanol | 50 | 50 | 50 | 50 | 50 |
| flavor | proper amt. | proper amt. | proper amt. | proper amt. | proper amt. |
| purified water | balance | balance | balance | balance | balance |
| pH control | 6~7 | 6~7 | 6~7 | 6~7 | 6~7 |

Notes
*1carboxyvinyl polymer (a product of Goodrich)
*2polyether-modified silicone
*3Piroctone Auramine (a product of Hoechst)

The scalp treatments A and B of the present invention and the comparative scalp treatments C, D and E were subjected to the same clinical test as that of Example 1 to examine their effectiveness in controlling the formation of dandruff and greasiness of the hair. The results are shown in Table 6.

TABLE 6

| Scalp treatment | Dandruff | Greasiness |
|---|---|---|
| A | 0.8 | 0.2 |
| B | 0.2 | 0.2 |
| C | 2.8 | 1.0 |
| D | 0.2 | 3.0 |
| E | 3.0 | 2.2 |

EXAMPLE 3

Hair conditioner A of the present invention and control B having the compositions shown in Table 7 were prepared.

TABLE 7

| Formulation | A | B |
|---|---|---|
| porous vinyl polymer prepared in Preparation Example 4 | 4.5 wt % | — |
| Octopirox | 0.3 | 0.3 |
| dialkyldimethylammonium chloride | 0.5 | 0.5 |
| stearyltrimethylammonium chloride | 1.0 | 1.0 |
| solid paraffin | 0.5 | 0.5 |
| liquid paraffin | 0.5 | 0.5 |
| polymethylsiloxane | 0.5 | 0.5 |
| methylcellulose | 0.5 | 0.5 |
| propylene glycol | 3.0 | 3.0 |
| stearyl alcohol | 3.0 | 3.0 |
| colorant | proper amt. | proper amt. |
| flavor | proper amt. | proper amt. |
| purified water | balance | balance |

EXAMPLE 4

Shampoo A of the present invention and control B having the compositions shown in Table 8 were prepared.

TABLE 8

| Formulation | A | B |
|---|---|---|
| fine particles of zeolite*1 | 5.0 wt % | — |
| Zpt | 1.0 | 1.0 |
| AS-TEA*2 | 20 | 20 |
| Carbopol 941 | 0.5 | 0.5 |
| urea | 5.0 | 5.0 |
| triethanolamine | 2.0 | 2.0 |
| thickening agent (Cellosize QP 52000H) | 0.1 | 0.1 |
| pigment | proper amt. | proper amt. |
| flavor | proper amt. | proper amt. |
| purified water | balance | balance |

Notes
*1average particle diameter: 0.8 μm (prepared by pulverizing ordinary zeolite with a sand grinder)
*2triethanolamine laurylsulfate

EXAMPLE 5

Hair preparations A, B and C of the present invention having the compositions shown in Table 9 were prepared.

TABLE 9

|  | Present invention | | |
|---|---|---|---|
|  | A | B | C |
| porous vinyl polymer prepared in Preparation Example 1 | 0.3 wt % | — | — |
| porous vinyl polymer prepared in Preparation Example 2 | — | 0.3 | — |
| porous vinyl polymer prepared in Preparation Example 3 | — | — | 0.3 |
| Carbopol 941 | 0.04 | 0.04 | 0.04 |
| l-menthol | 0.05 | 0.05 | 0.05 |
| 2,2'-dithiobispyridine 1,1'-dioxide | 0.1 | 0.1 | 0.1 |
| flavor | 0.2 | 0.2 | 0.2 |
| ethanol | 48 | 48 | 48 |
| water | balance | balance | balance |

In examples 3 to 5, the preparations of the present invention containing both the anti-dandruff agent and the oil-absorptive substance exhibited both anti-dandruff and greasiness reducing effects.

EXAMPLE 6

A paste hair preparation having the following composition was prepared:

| porous vinyl polymer prepared in Preparation Example 1 | 15 wt. % |
|---|---|
| carboxymethylcellulose | 0.5 |
| ethyl alcohol | 30 |
| flavor | 0.1 |
| water | q.s. ad 100 wt. % |

For comparison, paste hair preparations were prepared in the same manner as above except that the polymer prepared in Preparation Example 1 was replaced with Polymer No. 14 described in the specification of U.S. Pat. No. 4,489,058, talc or kaolin.

Each preparation was applied to the cheek of a subject and peeled off after one hour. The amount of sebum thus absorbed was determined by gravimetry.

The results are shown in Table 10.

TABLE 10

|  | Preparation of the present invention | Polymer No. 14 of U.S. Pat. No. 4,489,058 | Preparation comprising talc | Preparation comprising kaolin |
|---|---|---|---|---|
| Amount of sebum ($\mu g/cm^2$) | 18 ± 6 | 2 ± 1 | 12 ± 8 | 8 ± 6 |

It is apparent from Table 10 that the hair preparation of the present invention has a higher capacity of absorbing sebum than the comparative ones.

EXAMPLE 7

A hair preparation having the following composition was prepared:

| water-insoluble, porous vinyl polymer prepared in Preparation Example 2 | 0.3 wt. % |
|---|---|
| carboxyvinyl polymer (Carbopol 941; a product of Goodrich) | 0.04 |
| l-menthol | 0.05 |
| flavor | 0.2 |
| ethyl alcohol | 48 |
| purified water | q.s. ad 100 wt. % |

The hair preparation was applied to the hair on one side of the head of each of six subjects and a polymer-free preparation (comparative preparation) was applied to the hair on the other side. A difference in the greasiness between the both sides was examined organoleptically by monitors after one, two and three days.

The results are shown in Table 11.

TABLE 11

|  | After 1 day | | After 2 days | | After 3 days | |
|---|---|---|---|---|---|---|
| Subject | Present invention | Comp. | Present invention | Comp. | Present invention | Comp. |
| A | O | Δ | O | x | O | x |
| B | O | O | O | O | O | Δ |
| C | O | O | O | Δ | Δ | x |
| D | O | Δ | O | x | Δ | x |
| E | O | O | Δ | x | x | x |
| F | O | O | O | Δ | Δ | Δ |

Notes
O: nearly free from greasiness
Δ: slight greasiness
x: strong greasiness

EXAMPLE 8

A hair conditioner having the following composition was prepared:

| dispersion of porous vinyl polymer prepared in Preparation Example 3 (in terms of solid) | 1.0 wt. % |
|---|---|
| stearyltrimethylammonium chloride | 1.5 |
| cetanol | 2.3 |
| propylene glycol | 5.0 |
| methylparaben | 0.2 |
| hydroxyethylcellulose | 0.8 |
| Blue No. 1 | a suitable amount |
| flavor | " |
| purified water | the balance |

The hair conditioner was applied to hair on one side of the head of each of five subjects and a polymer-free comparative preparation was applied to hair on the other side. After washing with water, the greasiness was examined after one, two and three days in the same manner as that of Example 7.

The results are shown in Table 12.

TABLE 12

|  | After 1 day | | After 2 days | | After 3 days | |
|---|---|---|---|---|---|---|
| Subject | Present invention | Comp. | Present invention | Comp. | Present invention | Comp. |
| A | O | O | O | x | O | x |
| B | O | O | O | Δ | Δ | x |
| C | O | O | O | Δ | O | Δ |
| D | O | O | Δ | Δ | Δ | x |
| E | O | Δ | x | x | x | x |

We claim:

1. A hair preparation which comprises particles of an oil-absorptive polymer of a vinyl monomer having a solubility parameter of 7 to 10, said vinyl monomer being an ester of a higher alcohol having 8 to 24 carbon atoms, said particles having an average particle diameter of 0.005 to 30 μm and a pore volume of at least 0.1 ml/g, said polymer having a squalene absorption of at least 1 ml/g, and a carrier.

2. A hair preparation as claimed in claim 1, which comprises 0.05 to 5 percent by weight of the oil-absorptive polymer and the balance of the carrier.

3. A hair preparation as claimed in claim 1, in which said oil-absorptive polymer has 90 percent by weight or more of its particles in the size range of 0.005 to 30 microns.

4. A hair preparation as claimed in claim 1, in which said oil-absorptive polymer is crosslinked.

5. A hair preparation as claimed in claim 1, in which said polymer has a squalene absorption of at least 2 ml/g.

6. A hair preparation as claimed in claim 1, in which said particles are dispersed in a liquid selected from the group consisting of water, a lower alcohol and a mixture thereof.

7. A hair preparation as claimed in claim 1, in which said hair preparation contains an anti-dandruff agent.

8. A hair preparation as claimed in claim 1, in which said vinyl monomer is stearyl methacrylate.

9. A hair preparation as claimed in claim 1, in which said polymer is composed of monomer units of stearyl methacrylate and t-butylstyrene.

10. A hair preparation which comprises 0.01 to 10 percent by weight of an anti-dandruff agent, 0.05 to 5 percent by weight of an oil-absorptive substance in the form of fine particles and having a squalene absorption of at least 0.5 ml/g in the dried state and the balance of a carrier, said oil-absorptive substance being selected from the group consisting of a bentonite comprising montmorillonite and a porous vinyl ester, said vinyl ester being an ester of a higher alcohol having 8 to 24 carbon atoms.

11. A hair preparation as claimed in claim 10, in which said oil-absorptive substance is a porous vinyl polymer of a vinyl monomer having a solubility of 7 to 10, said particles have an average particle diameter of 0.005 to 30 μm and a pore volume of at least 0.1 ml/g. and said polymer has a squalene absorption of at least 1 ml/g.

* * * * *